(12) United States Patent
Akaweih (10) Patent No.: US 12,324,418 B2
(45) Date of Patent: Jun. 10, 2025

(54) PET DIAPER WITH DETACHABLE WASTE BAG

(71) Applicant: Nadia S. Akaweih, Houston, TX (US)

(72) Inventor: Nadia S. Akaweih, Houston, TX (US)

( * ) Notice: Subject to any disclaimer, the term of this patent is extended or adjusted under 35 U.S.C. 154(b) by 2 days.

(21) Appl. No.: 18/366,335

(22) Filed: Aug. 7, 2023

(65) Prior Publication Data

US 2025/0048997 A1   Feb. 13, 2025

(51) Int. Cl.
| | | |
|---|---|---|
| *A01K 23/00* | (2006.01) | |
| *A61F 13/15* | (2006.01) | |
| *A61F 13/42* | (2006.01) | |
| *A61F 13/505* | (2006.01) | |
| *A61F 13/84* | (2006.01) | |

(52) U.S. Cl.
CPC .............. *A01K 23/00* (2013.01); *A61F 13/42* (2013.01); *A61F 13/505* (2013.01); *A61F 13/84* (2013.01); *A61F 2013/15186* (2013.01); *A61F 2013/8402* (2013.01)

(58) Field of Classification Search
CPC ....................... A01K 23/00; A61F 2013/15186
See application file for complete search history.

(56) References Cited

U.S. PATENT DOCUMENTS

| | | | | |
|---|---|---|---|---|
| 3,656,459 | A * | 4/1972 | Missud | A01K 23/00 119/868 |
| 4,537,153 | A * | 8/1985 | Vidal | A01K 23/00 119/869 |
| 6,722,319 | B1 * | 4/2004 | Chiu | A01K 23/00 119/868 |
| 9,585,796 | B2 * | 3/2017 | Klofta | A61F 13/42 |
| 10,238,090 | B2 * | 3/2019 | Zoltanski | A01K 1/0152 |
| 11,090,200 | B2 * | 8/2021 | Qiu | A61F 13/495 |
| 11,229,189 | B2 * | 1/2022 | Komatsubara | B32B 5/18 |
| 11,330,801 | B2 * | 5/2022 | Landtved | A61B 10/007 |
| 11,564,377 | B2 * | 1/2023 | Martin | A01K 23/00 |
| 2010/0094235 | A1 * | 4/2010 | Solomon | A01K 23/00 119/869 |
| 2022/0346353 | A1 * | 11/2022 | Alexander | A01K 23/00 |
| 2023/0337633 | A1 * | 10/2023 | Beaupierre | A01K 23/00 |
| 2023/0413784 | A1 * | 12/2023 | Komatsubara | A61F 13/15756 |
| 2024/0269009 | A1 * | 8/2024 | Lin | A61F 13/42 |

FOREIGN PATENT DOCUMENTS

| | | |
|---|---|---|
| EP | 1570731 A1 | 9/2005 |
| GB | 2459867 A | 11/2009 |
| KR | 101744891 B1 | 6/2017 |

OTHER PUBLICATIONS

Pet Parents Brand, https://petparentsbrand.com/products/dog-diapers.

* cited by examiner

*Primary Examiner* — Kimberly S Berona
*Assistant Examiner* — Nevena Aleksic
(74) *Attorney, Agent, or Firm* — Nadia Akaweih; Maymanat Afshar (57) ABSTRACT

A pet diaper with detachable waste bag capable of collecting feces, in a detachable bag for easier collection and disposal enables a caretaker to easily remove the waste bag from the diaper for quick disposal without making a mess and without having to reach all the way to the ground. Furthermore, the pet diaper has a removable diaper core eliminating the need to change the entire diaper after the pet urinates.

5 Claims, 7 Drawing Sheets

PET DIAPER WITH DETACHABLE WASTE BAG

FIELD OF THE INVENTION

The present invention is directed to a pet diaper with detachable waste bag capable of collecting feces. In addition, the pet diaper with disposable waste bag can be configured with a removable diaper core eliminating the need to change the entire diaper after the pet urinates.

BACKGROUND OF THE INVENTION

Pet diapers can be used on various types of pets to include dogs, cats, monkeys, lemurs, horses, and even ducks. Pet diapers are typically made to collect urine or feces but not made to collect both in one diaper. There are even specialty pet diapers for female menstruation. However, there does not exist a diaper that is capable of collecting urine and feces that also takes into consideration the comfort of the pet and the caretaker. For example, if a caretaker has an elderly pet who has mobility issues, that caretaker has to use three separate diapers to ensure all of his/her pet's needs are being met. This can get expensive and cumbersome.

There are many types of pet breeds, sizes, and temperaments. Some pets prefer to be outdoors when they do their business. Some pets refuse to defecate in the diaper itself. This can be uncomfortable and unsanitary for the pet, not to mention messy for the pet's caretaker. Being able to easily remove the pet's feces without mess or hassle would be a welcome relief for the pet and his/her caretaker.

In case of a dog, some dog diapers have a flap intended to direct the dog's waste into the diaper when the dog is evacuating his/her bowels. However, in some of these diapers, when the dog's tail goes up, the flap falls down forcing the waste out of the diaper and on to the floor or ground.

In addition, people who have mobility issues like the elderly can find it difficult to reach all the way to the ground to pick up their pet's waste and properly dispose of it in a designated area. These types of people would benefit from a diaper with an easily removable waste bag.

A common issue with senior pets, in particular dogs, is incontinence which requires use of a dog diaper. Some senior dogs who suffer from incontinence can urinate nine to ten times a day. Using and disposing of paper diapers can be expensive and cumbersome on the caretaker and the waste management system.

In the alternative, while using reusable or cloth diapers may grant reprieve to the waste management system, it instead puts a strain on the caretaker's water and laundry bill. Currently, once a dog urinates in a reusable diaper, it must be changed and replaced. If not, the dog could suffer from urinary tract infections or sores. In one day, this could mean using nine or ten reusable diapers.

Therefore, there exists a need for a pet diaper that does not suffer from aforementioned problems and will provide a more efficient and easy to use pet diaper system.

SUMMARY OF THE INVENTION

The present invention is directed to a pet diaper with detachable waste bag capable of collecting feces. More specifically, the pet diaper with detachable waste bag enables a caretaker to easily remove the waste bag from the diaper for quick disposal without making a mess and without having to reach all the way to the ground. Furthermore, the pet diaper has a removable diaper core eliminating the need to change the entire diaper after the pet urinates.

In an exemplary embodiment, a diaper with detachable waste bag, comprises a diaper shell comprising an inner layer, an outer layer, a diaper first side, a diaper second side, a diaper third side, and a diaper fourth side; a diaper core; a tail hole; an evacuation hole comprising a plurality of third attachment points; a first strap comprising a first attachment point; a second strap comprising a second attachment point; a third strap comprising a first fastener; a fourth strap comprising a second fastener; and a waste bag attachment mechanism comprising an attachment bottom, an attachment top, a bag holder, a plurality of third fasteners, and at least one waste bag. In an embodiment, the plurality of third fasteners are permanently attached to the attachment bottom and the waste bag attachment mechanism is removably attached to the evacuation hole by securing the plurality of third fasteners to the plurality of the third attachment points.

In one embodiment, the diaper core is permanently attached to the inner layer. In an alternate embodiment, the diaper core is removable from the inner layer. In yet another embodiment, the diaper core comprises a wetness indicator.

In an embodiment, the material of construction for the diaper core comprises a super absorbent material capable of absorbing urine such as bleached rayon, cotton, plastic, or any combination thereof.

In another embodiment, the material of construction of the first fastener, the second fastener, the third fastener, the first attachment point, the second attachment point, and the third attachment point comprises hook and loop tape, temporary adhesive, snap fasteners, buttons, or any combination thereof.

In yet another embodiment, the material of construction for the first strap, the second strap, the third strap, and the fourth strap comprises an elastic material capable of stretching to accommodate varying pet girths such as elastin, rubber, nylon, lycra, latex, gum, elastic band, graphene, or any combination thereof.

In an alternate embodiment, the waste bag is expandable.

In another embodiment, the material of construction of the diaper with detachable waste bag comprises cloth, cotton, wool, bamboo, hemp, microfiber, polyester, polyurethane laminate, or any combination thereof.

In an alternate embodiment, the material of construction of the diaper with detachable waste bag comprises material capable of being disposable such as paper, polyethylene film, superabsorbent polymers, nonwoven material, or any combination thereof.

In another embodiment, the material of construction for waste bag attachment mechanism comprises plastic, rubber, or any combination thereof.

In an exemplary embodiment, a method of using a diaper with detachable waste bag comprises the following steps for securing the diaper with detachable waste bag to a dog by: (1) laying the diaper fourth side along back of the dog ensuring the inner layer is touching the dog; (2) pulling tail of the dog through the tail hole ensuring the tail is located on the outer surface of the diaper; (3) pulling the diaper third side through the legs of the dog ensuring the diaper third side rests on the stomach of the dog; (4) securing the first fastener of the third strap to the first attachment point of the first strap creating a loop with the diaper first side around one of the hind legs of the dog; and (5) securing the second fastener of the fourth strap to the second attachment point of the second strap creating a loop with the diaper second side around the other of the hind legs of the dog.

In another embodiment, a method of using a diaper with detachable waste bag comprises the following steps for removing and replacing the diaper core by: (1) detaching the first fastener of the third strap from the first attachment point of the first strap; (2) detaching the second fastener of the fourth strap from the second attachment point of the second strap; (3) removing the diaper core from the inner layer of the diaper shell; (4) replacing the diaper core by removably attaching the diaper core to the inner layer of the diaper shell; (5) securing the first fastener of the third strap to the first attachment point of the first strap creating a loop with the diaper first side around one of the hind legs of the dog; and (6) securing the second fastener of the fourth strap to the second attachment point of the second strap creating a loop with the diaper second side around the other of the hind legs of the dog.

Various objects, features, aspects, and advantages of the inventive subject matter will become apparent from the following detailed description of exemplary embodiments, along with the accompanying figures in which like numerals represent like components.

DETAILED DESCRIPTION OF THE INVENTION

The following description is not an admission that any of the information provided herein is prior art or relevant to the present invention, or that any publication specifically or implicitly referenced is prior art. Any publications cited in the description are incorporated by reference herein. Where a definition or use of a term in an incorporated reference is inconsistent or contrary to the definition of that term provided herein, the definition of that term provided herein applies and the definition of that term in the reference does not apply.

As used in the description herein and throughout the claims that follow, the meaning of "a," "an," and "the" includes plural reference unless the context clearly dictates otherwise. Also, as used in the description herein, the meaning of "in" includes "into" and "on" unless the context clearly dictates otherwise.

As used herein, the terms "pet diaper with detachable waste bag," "pet diaper," and "diaper" are used interchangeably throughout the disclosure.

The present invention is directed to a pet diaper with a detachable waste bag. The waste bag attachment mechanism is capable of holding at least one waste bag and is configured to be removable without taking the entire diaper off the pet. Additionally, a removable diaper core is configured to absorb urine and can be removed and replaced after use without replacing the entire diaper.

The pet diaper with detachable waste bag can be constructed to accommodate different sizes of pets. For example, an extra small diaper could fit a small pet like a Chihuahua and an extra-large diaper could fit a big pet like an English Mastiff. Additionally, the diaper bag comprises a plurality of straps capable of stretching over each other for a more secure fit around the girth of the pet.

In one embodiment, the pet diaper is configured to be reusable and washable after use. In another embodiment, the pet diaper is configured to be disposable after use.

Exemplary configurations of the present invention are depicted in FIGS. 1 to 4, 5A, 5B, 5C, 5D, 6, and 7 in which pet diaper 100 is configured to easily collect the pet's feces outside of the diaper without the feces falling to the ground.

Figure 1:
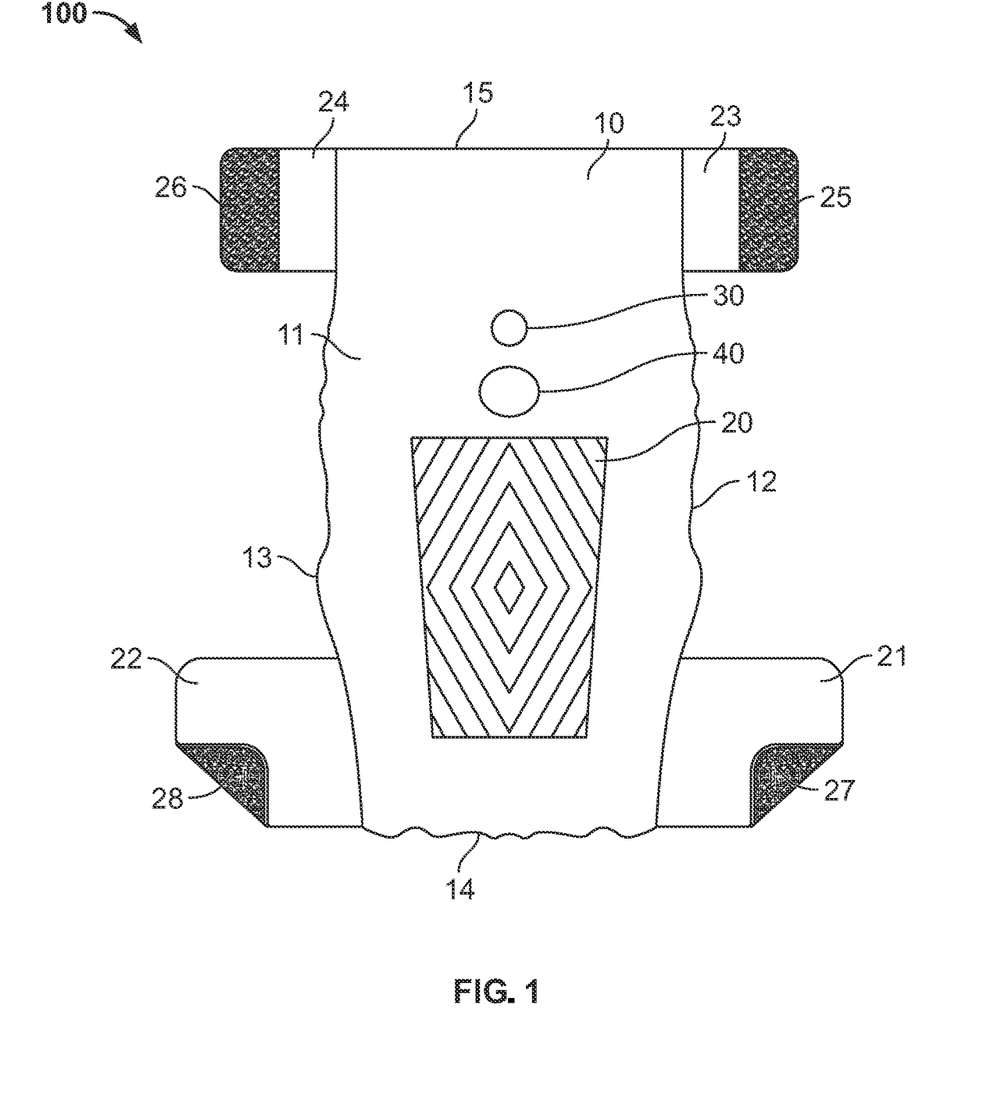
FIG. 1 depicts the front view of an exemplary embodiment of a pet diaper with detachable waste bag.
Figure 2:
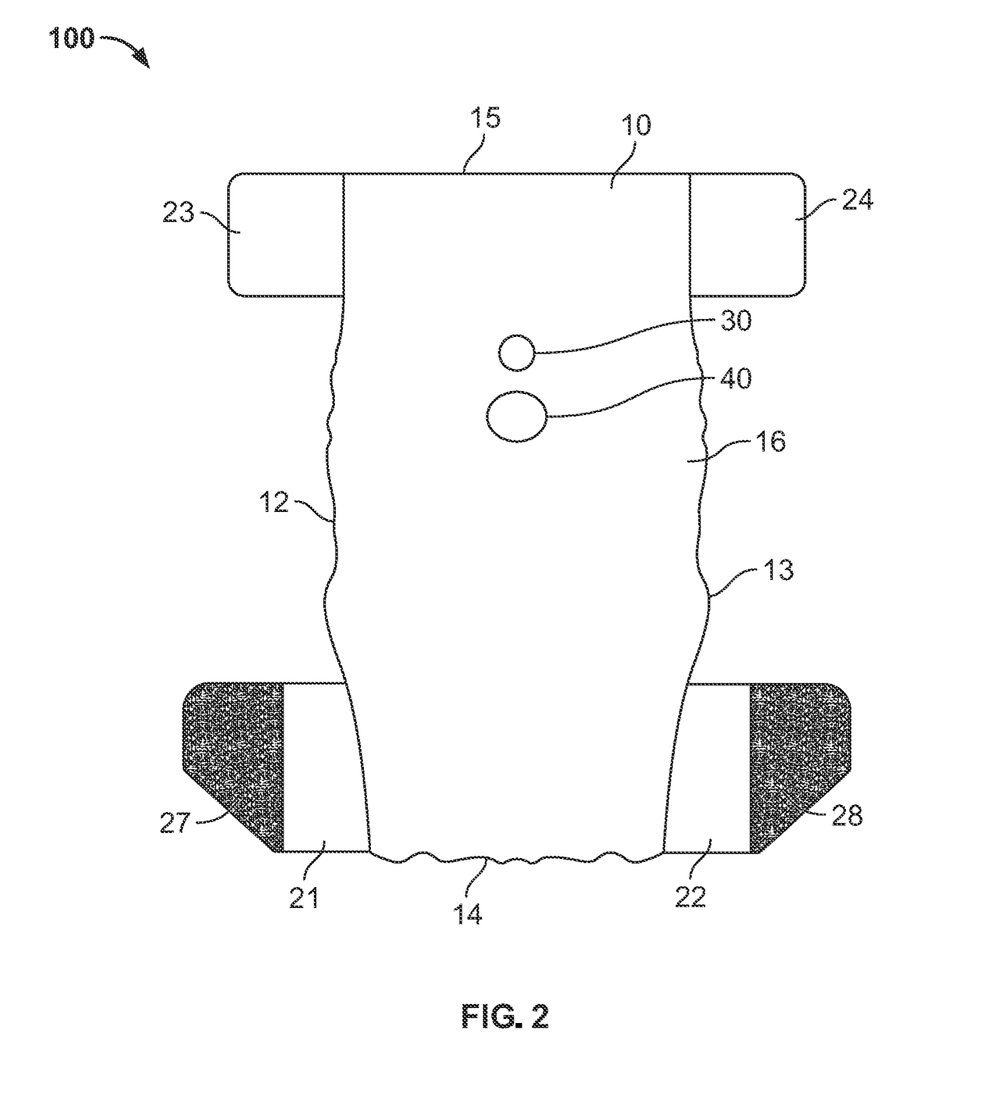
FIG. 2 depicts the back view of an exemplary embodiment of a pet diaper with detachable waste bag.
Figure 3:
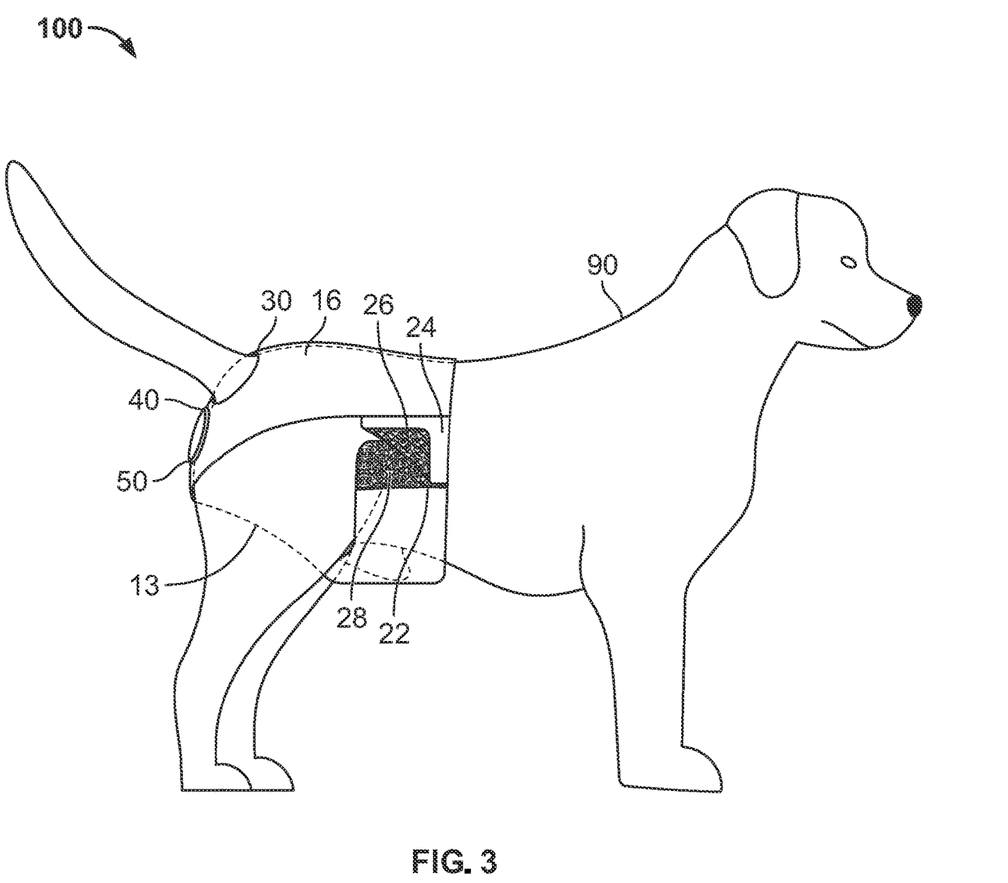
FIG. 3 depicts the perspective view of an exemplary embodiment of a pet diaper with detachable waste bag in use on a dog.
Figure 4:
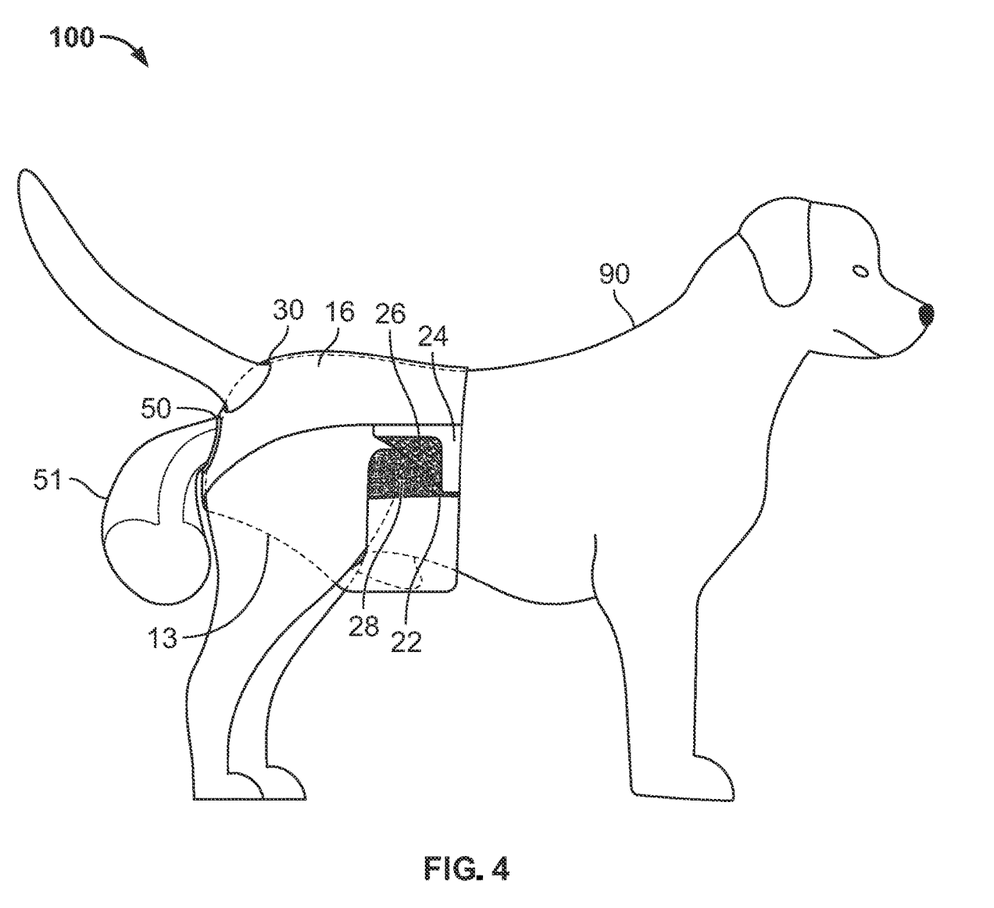
FIG. 4 depicts the perspective view of an exemplary embodiment of a pet diaper with detachable waste bag in use on a dog with the waste bag extended.

FIGS. 1 to 3 depict an exemplary embodiment of pet diaper with detachable waste bag 100 comprising diaper shell 10, diaper core 20, tail hole 30, evacuation hole 40, waste bag attachment mechanism 50, first strap 21, second strap 22, third strap 23, and fourth strap 24. In an exemplary embodiment, diaper shell 10 comprises inner layer 11, diaper first side 12, diaper second side 13, diaper third side 14, diaper fourth side 15, and outer layer 16.

In this embodiment, first strap 21 comprises first attachment point 27, second strap 22 comprises second attachment point 28, third strap 23 comprises first fastener 25, and fourth strap 24 comprises second fastener 26, wherein first attachment point 27 is fixedly attached to first strap 21, second attachment point 28 is fixedly attached to second strap 22, first fastener 25 is fixedly attached to third strap 23, and second fastener 26 is fixedly attached to fourth strap 24.

In one embodiment, diaper core 20 is permanently affixed to inner layer 11. In this embodiment, diaper core 20 comprises a wetness indicator covering the entirety of diaper core 20. The wetness indictor changes colors when diaper 100 is wet signaling to the caretaker that the pet has urinated. This technology is known in the art. For example, U.S. Pat. No. 9,585,796 discloses absorbent articles comprising wetness indicators.

In an alternate embodiment, diaper core 20 is removably attached to inner layer 11 and is configured to absorb urine to minimize leaks. In this embodiment, diaper core 20 further comprises a wetness indicator for signaling to pet's caretaker when diaper core 20 is full of urine. Diaper core 20 can be removed and disposed of after each use. In an embodiment, a new diaper core 20 is replaced without entire pet diaper 100 being replaced (see FIG. 7).

In an embodiment, material of construction for diaper core 20 comprises a super absorbent material capable of absorbing urine such as bleached rayon, cotton, plastic, or any combination thereof.

In one embodiment, the method for securing pet diaper with detachable waste bag 100 to dog 90 comprises the following steps. Step 1 comprises laying diaper fourth side 15 along the back of dog 90 so inner layer 11 is touching dog 90. Step 2 comprises pulling tail of dog 90 through tail hole 30 so the tail is on the outer surface of diaper 100. Step 3 comprises pulling diaper third side 14 through the legs of dog 90 so diaper third side 14 rests on the stomach of dog 90. Step 4 comprises securing first fastener 25 of third strap 23 to first attachment point 27 of first strap 21 creating a loop with diaper first side 12 around one of the hind legs of dog 90. Step 5 comprises securing second fastener 26 of fourth strap 24 to second attachment point 28 of second strap 22 creating a loop with diaper second side 13 around the other of the hind legs of dog 90 (see FIG. 3).

In one embodiment, material of construction for first fastener 25, second fastener 26, first attachment point 27, and second attachment point 28 comprises hook and loop tape. In an alternate embodiment, first fastener 25, second fastener 26, first attachment point 27, and second attachment point 28 comprises adhesive tape. In yet another embodiment, first fastener 25, second fastener 26, first attachment point 27, and second attachment point 28 comprises snap fasteners, buttons, or any combination thereof.

In an embodiment, material of construction for first strap 21, second strap 22, third strap 23, and fourth strap 24 comprises an elastic material capable of stretching to accommodate the varying girths of dog 90. In an embodiment, material of construction for first strap 21, second strap 22, third strap 23, and fourth strap 24 comprises elastin, rubber, nylon, lycra, latex, gum, elastic band, graphene, or any combination thereof.

FIG. 3 depicts the perspective view of an exemplary embodiment of pet diaper 100 in use on dog 90. In an exemplary embodiment, waste bag attachment mechanism 50 is removably attached to pet diaper 100 via hook and loop tape. In this embodiment, waste bag attachment mechanism 50 comprises attachment top 53, attachment bottom 52, bag holder 54, at least one waste bag 51, and a plurality of third fastener 55. Evacuation hole 40 comprises a plurality of third attachment points 56, wherein a plurality of third fasteners 55 are removably attached to a plurality of corresponding third attachment points 56 on evacuation hole 40 (see FIGS. 5A, 5B, 5C, 5D, and 6).

In one embodiment, waste bag attachment mechanism 50 is in a retracted state until the pet evacuates his/her bowels. In this embodiment, at least one waste bag 51 is flattened within bag holder 54. In an alternate embodiment, three to five of waste bag 51 lay flat within bag holder 54. In an embodiment, waste bag 51 expands from bag holder 54 by the motion of the tail and the force of the waste extending from dog 90 (see FIG. 4). Once dog 90 has finished defecating, waste bag 51 is removable from waste bag attachment mechanism 50.

Figure 5A:
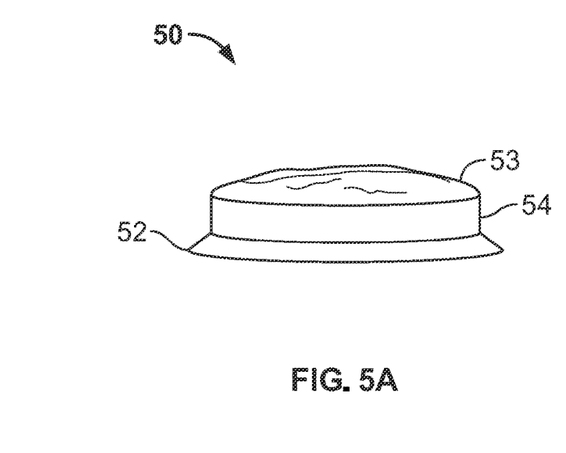
FIG. 5A depicts the side view of an exemplary embodiment of the waste bag attachment mechanism.
Figure 5B:
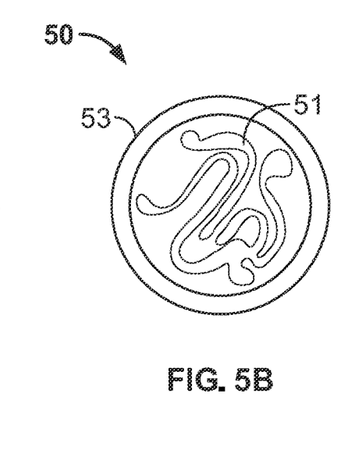
FIG. 5B depicts the top view of an exemplary embodiment of the waste bag attachment mechanism.
Figure 5C:
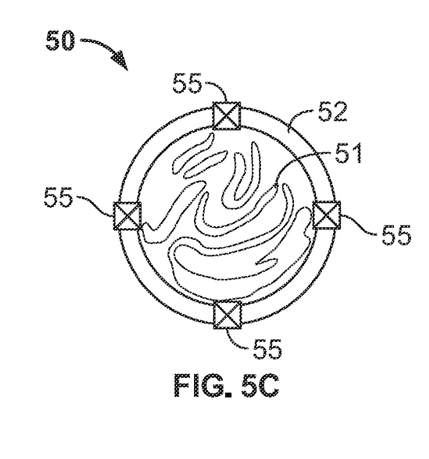
FIG. 5C depicts the bottom view of an exemplary embodiment of the waste bag attachment mechanism.

In an exemplary embodiment, waste bag attachment mechanism 50, comprises at least one waste bag 51, attachment bottom 52, attachment top 53, bag holder 54, and a plurality of third fastener 55 (see FIGS. 5A, 5B, 5C). In this embodiment, evacuation hole 40 comprises a plurality of third attachment points 56. In one embodiment, the plurality of third fastener 55 is removably attached to third attachment point 56 securing attachment bottom 52 to evacuation hole 40.

In an exemplary embodiment, material of construction for third fastener 55 and third attachment point 56 comprises hook and loop tape, adhesive, snap fasteners, buttons, or any combination thereof.

FIG. 5B depicts the top view of an exemplary embodiment of waste bag attachment mechanism 50, wherein bag holder 54 comprises at least one waste bag 51. In this embodiment, waste bag 51 is temporarily secured within bag holder 54 until dog 90 evacuates his/her bowels.

FIG. 5C depicts the side view of an exemplary embodiment of waste bag attachment mechanism 50, wherein attachment bottom 52 comprises a plurality of third fasteners 55.

Figure 5D:
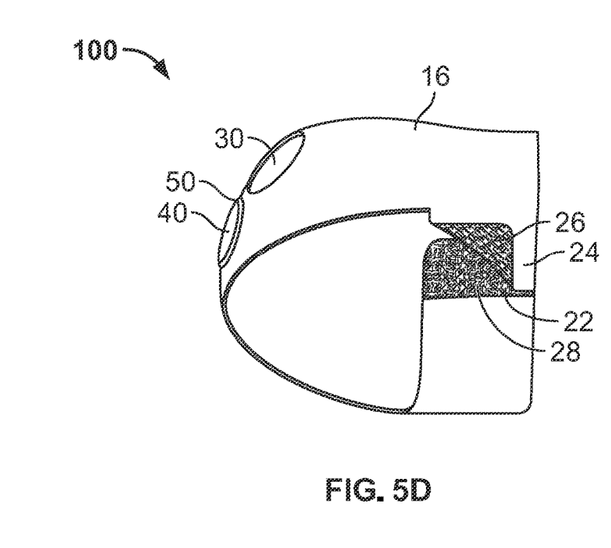
FIG. 5D depicts the perspective view of an exemplary embodiment of a pet diaper with detachable waste bag shown with the waste bag attachment mechanism attached to the diaper.

FIG. 5D depicts the perspective view of an exemplary embodiment of pet diaper with detachable waste bag 100, wherein waste bag attachment mechanism 50 is temporarily secured to evacuation hole 40.

Figure 6:
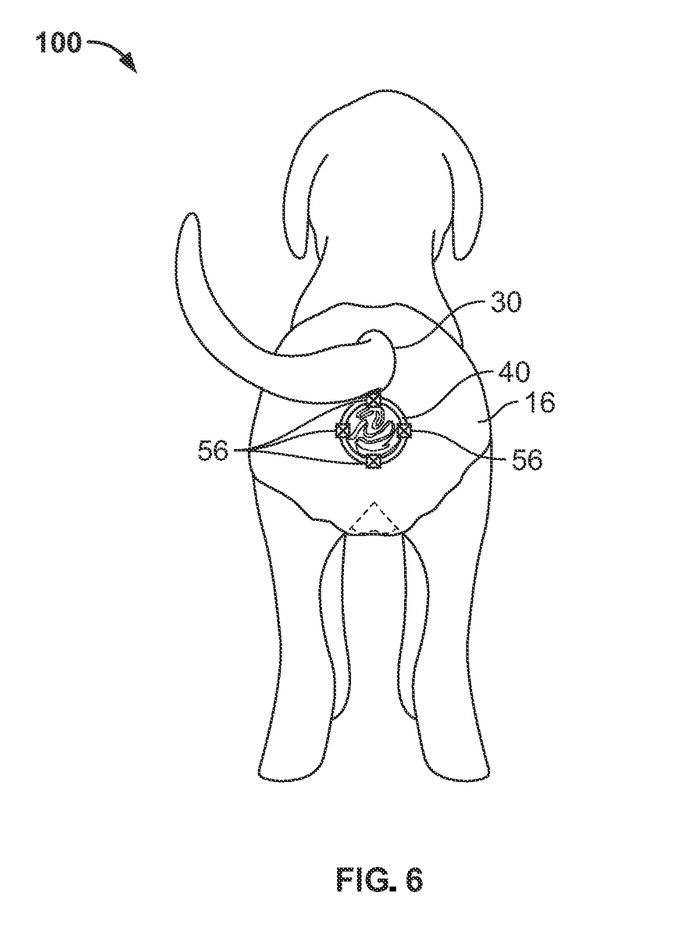
FIG. 6 depicts the perspective view of an exemplary embodiment of a pet diaper with detachable waste bag shown with the bag mechanism attachment points.
Figure 7:
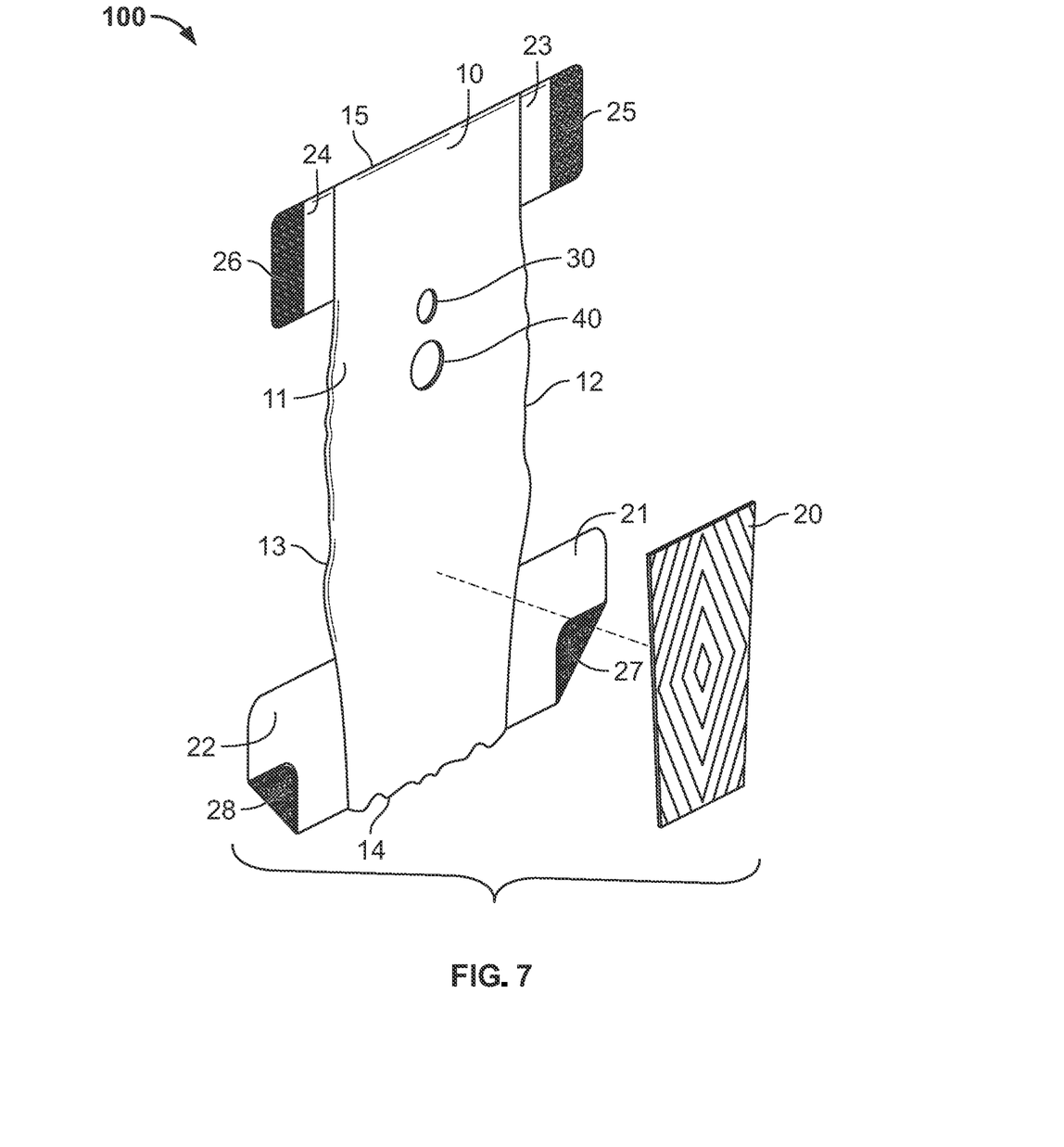
FIG. 7 depicts the perspective view of an exemplary embodiment of a pet diaper with detachable waste bag shown with a removable diaper core.

FIG. 6 depicts the perspective view of an exemplary embodiment of pet diaper with detachable waste bag 100 comprising a plurality of third attachment points 56. In this embodiment, waste bag attachment mechanism 50 is removably attached to diaper 100 by securing plurality of third fasteners 55 on waste bag attachment mechanism 50 to third attachment point 56 on pet diaper 100.

In one embodiment, material of construction for diaper with detachable waste bag 100 comprises resilient durable material such as cloth, cotton, wool, bamboo, hemp, microfiber, polyester, polyurethane laminate, or any combination thereof.

In another embodiment, material of construction for diaper with detachable waste bag 100 comprises resilient durable material capable of being disposable such as paper, polyethylene film, superabsorbent polymers, nonwoven material, or any combination thereof. Material of construction for waste bag attachment mechanism 50 comprises plastic, rubber, or any combination thereof. One of ordinary skill in the art can envision other types of material of construction for diaper 100 and waste bag attachment mechanism 50 that are within the scope of the present invention.

Thus, specific embodiments of a diaper with detachable waste bag and method of use have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The invention claimed is:

1. A diaper with detachable waste bag, comprising:
   a. a diaper shell comprising an inner layer, an outer layer, a diaper first side, a diaper second side, a diaper third side, and a diaper fourth side;
   b. a diaper core, wherein said diaper core is removably attached to said inner layer of said diaper shell;
   c. a tail hole;
   d. an evacuation hole comprising a plurality of third attachment points, wherein said third attachment points readily accept a waste bag attachment mechanism;
   e. a first strap comprising a first attachment point;
   f. a second strap comprising a second attachment point;
   g. a third strap comprising a first fastener;
   h. a fourth strap comprising a second fastener; and
   i. said waste bag attachment mechanism comprising an attachment bottom, an attachment top, a bag holder, a plurality of third fasteners, and at least one waste bag, wherein said plurality of third fasteners are permanently attached to said attachment bottom and said waste bag attachment mechanism is removably attached to said evacuation hole by securing said plurality of third fasteners to said plurality of said third attachment points.

2. The diaper with detachable waste bag as recited in claim 1, wherein said diaper core comprises a wetness indicator.

3. The diaper with detachable waste bag as recited in claim 1, wherein material of construction for said diaper core comprises a super absorbent material capable of absorbing urine such as bleached rayon, cotton, plastic, or any combination thereof.

4. The diaper with detachable waste bag as recited in claim 1, wherein said waste bag is expandable through said waste bag attachment mechanism as said waste bag is filled, wherein said waste bag is capable of being removed from said waste bag attachment mechanism.

5. The diaper with detachable waste bag as recited in claim 1, wherein material of construction for waste bag attachment mechanism comprises plastic, rubber, or any combination thereof.

\* \* \* \* \*